(12) United States Patent
Salahi (10) Patent No.: US 12,197,863 B2
(45) Date of Patent: Jan. 14, 2025

(54) METHODS AND SYSTEMS FOR PROCESSING DOCUMENTS WITH TASK-SPECIFIC HIGHLIGHTING

(71) Applicant: Amazon Technologies, Inc., Seattle, WA (US)

(72) Inventor: Murad Mehmet Salahi, San Jose, CA (US)

(73) Assignee: Amazon Technologies, Inc., Seattle, WA (US)

( * ) Notice: Subject to any disclaimer, the term of this patent is extended or adjusted under 35 U.S.C. 154(b) by 726 days.

(21) Appl. No.: 17/317,514

(22) Filed: May 11, 2021

(65) Prior Publication Data

US 2021/0357634 A1 Nov. 18, 2021

Related U.S. Application Data

(60) Provisional application No. 63/025,054, filed on May 14, 2020.

(51) Int. Cl.
| | |
|---|---|
| *G06K 9/00* | (2022.01) |
| *G06F 18/2413* | (2023.01) |
| *G06F 40/109* | (2020.01) |
| *G06F 40/284* | (2020.01) |
| *G06N 20/00* | (2019.01) |
| *G06V 10/46* | (2022.01) |
| *G06V 30/41* | (2022.01) |
| *G06V 30/413* | (2022.01) |
| *G16H 15/00* | (2018.01) |

(52) U.S. Cl.
CPC ........ *G06F 40/284* (2020.01); *G06F 18/2413* (2023.01); *G06F 40/109* (2020.01); *G06N 20/00* (2019.01); *G06V 10/464* (2022.01); *G06V 30/41* (2022.01); *G06V 30/413* (2022.01); *G16H 15/00* (2018.01)

(58) Field of Classification Search
None
See application file for complete search history.

(56) References Cited

U.S. PATENT DOCUMENTS

| | | | |
|---|---|---|---|
| 2019/0130073 A1* | 5/2019 | Sun | G16H 10/60 |
| 2020/0327194 A1* | 10/2020 | Tan | G06F 40/166 |
| 2021/0065191 A1* | 3/2021 | De Shetler | G06N 20/00 |
| 2021/0074398 A1* | 3/2021 | Fong | G16H 15/00 |

* cited by examiner

*Primary Examiner* — Wei Wen Yang
(74) *Attorney, Agent, or Firm* — Sheppard Mullin Richter & Hampton LLP (57) ABSTRACT

Methods and systems for automatically processing a document may include classifying a document, such as a medical document, as one or more document types based at least in part on one or more machine learning models and one or more tokens extracted from the medical document, determining a token contribution weight of each token towards the classification, modifying the medical document based on the token contribution weights of the one or more tokens, and displaying the modified medical document on a display to a user.

20 Claims, 9 Drawing Sheets
(2 of 9 Drawing Sheet(s) Filed in Color)

```
GI MEDS REPORT Patient ID: XXXXXXX
Procedure(s): Colonoscopy (11/14/2018 7:17:40 AM) Exam Date: 11/14/18
Account#: XXXX
Exam Date: 11/14/18 Patient ID: XXXX Doctor: XXXXX
Patient Name: XXXXXX DOB: XX/XX/XXXX Gender: Female Pre-Procedure / Active Medications
Discharge Comment
Anticoagulant use - Patient Denies Use Aspirin use - Patient Denies Use
Herbal use - Patient Denies Use
NSAID use - Patient Denies Use
pentasa 2tab po tid Last Taken Yesterday Confirmed 11/14/2018 Continue as prescribed Rowasa Rectal Enema 4 GM/60ML 4 GM/60ML Rectal Confirmed 11/14/2018 Continue as prescribed
nightly Last Taken Last Month simvastatin 20mg po daily Last Taken Last Month Confirmed 11/14/2018 Continue as prescribed

ALLERGIES

Food Allergy - Patient Denies Allergy
Iodine Allergy - Patient Denies Allergy
```

Two biopsies were taken every 10 cm with a cold forceps from the cecum, ascending colon, transverse colon, descending colon, sigmoid colon, rectum and rectosigmoid colon for Crohn's disease surveillance.
These biopsy specimens were sent to Pathology.
A 9 mm polyp was found in the mid sigmoid colon.
The polyp was semi-pedunculated.
The polyp was removed with a hot snare.
Resection and retrieval were complete.
The 9 mm sigmoid polyp had a mixed gross appearance of polypoid/inflammatory changes.
After snare polypectomy, it was bleeding and a clip was placed at the peduncle of the polyp.
Surronding tissue had mild colitis.
No deep ulceration was seen anywhere in her colon.
Ascending colon and rectum appeared fairly normal.
Powered by Provation MD Page 1 of 3 XXXXXXXX 56y F Patient Chart Report 04/24/19 6:42 pm DOB: XX/XX/XX Health Center Lab Facility: LabCorp of America Provider: XXXXXXXX Requisition: XXXXXXX Specimen: XXXXXX Collection Date: 03/15/19 Patient Lab Results Report Date: 03/16/19 Hemoglobin A1c Reviewed: 03/27/19 -Specimen Information- Specimen ID: 1 Collection Start Date: 03/15/2019 8:43 A Component Flag Result Units Range Status Hemoglobin A1c H 6.1 % 4.8-5.6 F Prediabetes: 5.7 - 6.4 Diabetes: >6.4 Glycemic control for adults with diabetes: <7.0 XXXXXXXXX 56y F Patient Chart Report 04/24/19 6:42 pm DOB: 01/27/63 Mount Vernon Neighborhood Health Center Lab Facility: LabCorp of America Provider: XXXXXXXXXXXX Requisition: XXXXXXXX Specimen: XXXXXXXX Collection Date: 03/15/19 Patient Lab Results Report Date: 03/16/19 Comp.
Metabolic Panel (14) Reviewed: 03/27/19 -Specimen Information- Specimen ID: 1 Collection Start Date: 03/15/2019 8:43 A Component Flag Result Units Range Status Glucose H 113 mg/dL 65-99 F BUN 13 ng/dL 6-24 F Creatinine 0.70 mg/dL 0.57-1.00 F eGFR If NonAfricn Am 97 mL/min/1.73 >59 F eGFR If Africn Am 112 mL/min/1.73 >59 F BUN/Creatinine Ratio 19 9-23 F Sodium 143 mmol/L 134-144 F Potassium 4.2 mmol/L 3.5-5.2 F Chloride 104 mmol/L 96-106 F Carbon Dioxide, Total 25 mmol/L 20-29 F Calcium 9.1 mg/dL 8.7-10.2 F Protein, Total 6.8 g/dL 6.0-8.5 F Albumin 4.1 g/dL 3.5-5.5 F Globulin, Total 2.7

FIG. 5A

Two biopsies were taken every 10 cm with a cold forceps from the cecum, ascending colon, transverse colon, descending colon, sigmoid colon, rectum and rectosigmoid colon for Crohn's disease surveillance.

These biopsy specimens were sent to Pathology.

A 9 mm polyp was found in the mid sigmoid colon.

The polyp was semi-pedunculated.

The polyp was removed with a hot snare.

Resection and retrieval were complete.

The 9 mm sigmoid polyp had a mixed gross appearance of polypoid/inflammatory changes.

After snare polypectomy, it was bleeding and a clip was placed at the peduncle of the polyp.

Surrounding tissue had mild colitis.

No deep ulceration was seen anywhere in her colon.

Ascending colon and rectum appeared fairly normal.

Powered by Provation MD Page 1 of 3 XXXXXXXX 55y F Patient Chart Report 04/24/19 8:42 pm DOB: XX/XX/XX Health Center Lab Facility: LabCorp of America Provider: XXXXXXX Requisition: XXXXXX Specimen: XXXXXXX Collection Date: 03/15/2019 8:45 A Component Flag Results Report Date: 03/15/19 Hemoglobin A1c Performed: 03/27/19 -Specimen Information– Specimen ID: 1 Collection Start Date: 03/15/2019 8:45 A Component Flag Result Units Range Status Hemoglobin A1c H 8.1 % 4.8-5.6 F Prediabetes: 5.7 - 6.4 Diabetes: >6.4 Glycemic control for adults with diabetes: <7.0 XXXXXXXX 55y F Patient Chart Report 04/24/19 8:42 pm DOB: 01/27/63 Mount Vernon Neighborhood Health Center Lab Facility: LabCorp of America Provider: XXXXXXXXXXXXX Requisition: XXXXXXXX Specimen: XXXXXXX Collection Date: 03/15/19 Patient Lab Results Report Date: 03/18/19 Comp. Metabolic Panel (14) Reviewed: 03/27/19 -Specimen Information– Specimen ID: 1 Collection Start Date: 03/15/2019 8:43 A Component Flag Result Units Range Status Glucose H 113 mg/dL 65-99 F BUN 13 mg/dL 6-24 F Creatinine 0.70 mg/dL 0.57-1.00 F eGFR If NonAfricn Am 97 mL/min/1.73 >59 F eGFR If Afrcn Am 112 mL/min/1.73 >59 F BUN/Creatinine Ratio 19 9-20 F Sodium 143 mmol/L 134-144 F Potassium 4.2 mmol/L 3.5-5.2 F Chloride 104 mmol/L 96-108 F Carbon Dioxide, Total 25 mmol/L 20-29 F Calcium 9.1 mg/dL 8.7-10.2 F Protein, Total 6.8 g/dL 6.0-8.5 F Albumin 4.1 g/dL 3.5-5.5 F Globulin, Total 2.7

METHODS AND SYSTEMS FOR PROCESSING DOCUMENTS WITH TASK-SPECIFIC HIGHLIGHTING

CROSS-REFERENCE TO RELATED APPLICATIONS

This application claims priority to U.S. Patent Application Ser. No. 63/025,054 filed May 14, 2020, which is incorporated herein in its entirety by this reference.

TECHNICAL FIELD

This invention relates generally to the field of processing documents, such as medical documents.

BACKGROUND

Medical records, in either physical or digital format, typically contain a deluge of information collected linearly over time. A patient's "chart" may contain any number of healthcare-related information, such as patient characteristics (e.g., age, sex, gender, weight, BMI, race, ethnicity, location, referrals, health insurance, etc.), medical events (e.g., diagnostics tests, imaging, treatments, prescriptions, etc.), and/or other relevant facts. Processing this massive amount of information is a crucial part of any medical institution's workflow, yet is a major time- and resource-consuming step for clinicians.

Furthermore, conventional manual methods for processing documents may result in mistakes, such as due to human error. Errors in identifying and classifying precise medical events from medical records can have serious implications for patient care, as well as the clinician's and/or medical institution's ability to accurately monitor key healthcare metrics, such as the National Committee for Quality Assurance's Healthcare Effectiveness Data and Information Set (HEDIS).

Accordingly, there is a need for new and improved methods and systems for automatically processing documents.

SUMMARY

Generally, in some variations, a method for automatically processing a medical document (or other suitable document) includes, at one or more processors, classifying a medical document as one or more document types based at least in part on one or more machine learning models and one or more tokens extracted from the medical document, determining a token contribution weight of each token toward the classification, modifying the medical document based on the token contribution weights of the one or more tokens, and displaying the modified medical document on a display to a user. In some variations, the method may further include classifying the medical document as including text relating to a particular medical event, such as a clinical exam.

In some variations, classifying the medical document may include determining at least one bag of words vector from one or more extracted tokens, generating at least one topic vector from the at least one bag of words vector, wherein the at least one topic vector comprises one or more topic features, each topic feature mapping to a probability distribution of tokens for the topic feature, and classifying the medical document based on the at least one topic vector. In some variations, generating at least one topic vector may include, for example, fitting a Latent Dirichlet Allocation model to the at least one bag of words vector. In some variations, classifying the medical document may include, for example, applying a gradient boosting classifier model to the at least one topic vector.

In some variations, determining a token contribution weight of each token may include determining an impact score associated with each topic feature in the at least one topic vector, distributing the impact scores to the one or more tokens according to the probability distributions mapped to each topic feature in the at least one topic vector, and determining the token contribution weight for each token by summing the distributed impact scores for the token. In some variations, the impact score may be, for example, a Shapley Additive Explanation (SHAP) value. In some variations, distributing the impact scores to the one or more tokens may include distributing the SHAP value of each topic feature to all of the one or more tokens, and normalizing the distributed SHAP values.

In some variations, modifying the medical document based on the token contribution weights may include mapping the token contribution weights to a color map, and modifying text of the medical document based on the mapping. Modifying the medical document may include changing, for example, at least one of text font appearance and text font highlighting based on the mapping. In some variations, modifying the medical document may include scaling the color map based on a confidence level of the classification of the medical document. In some variations, modifying the medical document comprises determining a sentence contribution weight of each sentence in the medical document based on the sum of token contribution weights of one or more tokens in the sentence, and mapping the sentence contribution weights to a color map.

In some variations, a method for automatically processing a medical document, includes determining a Healthcare Effectiveness Data and Information Set (HEDIS) quality metric based at least in part on the classification of the medical document.

Furthermore, a system for automatically processing a medical document, may include one or more processors configured to classify a medical document as one or more document types based at least in part on one or more machine learning models and one or more tokens extracted from the medical document, determine a token contribution weight of each token toward the classification, modify the medical document based on the token contribution weights of the one or more tokens, and display the modified medical document on a display to a user.

In some variations, the one or more processors is configured to classify the medical document at least in part by determining at least one bag of words vector from one or more extracted tokens, generating at least one topic vector from the at least one bag of words vector, wherein the at least one topic vector comprises one or more topic features, each topic feature mapping to a probability distribution of tokens for the topic feature, classifying the medical document based on the at least one topic vector.

In some variations, the one or more processors is configured to determine the token contribution weight of each token at least in part by determining an impact score associated with each topic feature in the at least one topic vector, distributing the impact scores to the one or more tokens according to the probability distributions mapped to each topic feature in the at least one topic vector, and determining the token contribution weight for each token by summing the distributed impact scores for the token.

In some variations, the one or more processors is configured to modify the medical document at least in part by mapping the token contribution weights to a color map and modifying text of the medical document based on the mapping. In some variations, the one or more processors is configured to modify the medical document at least in part by changing at least one of text font appearance and text font highlighting based on the mapping. In some variations, the one or more processors is configured to modify the medical document at least in part by determining a sentence contribution weight of each sentence in the medical document based on the sum of token contribution weights of one or more tokens in the sentence and mapping the sentence contribution weights to a color map.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 5A and 5B depict an example of an unprocessed medical document and a processed medical document with task-specific highlighting, respectively.

DETAILED DESCRIPTION

Non-limiting examples of various aspects and variations of the invention are described herein and illustrated in the accompanying drawings.

Described below are methods and systems for automatically processing a document, which may include classifying a document, such as a medical document, as one or more document types based at least in part on one or more machine learning models and one or more tokens extracted form the medical document, determining a token contribution weight of each token towards the classification, modifying the medical document based on the token contribution weights of the one or more tokens, and displaying the modified medical document on a display to a user.

The methods and systems described in the present disclosure improve efficiency by clinicians in classifying medical documents. For example, a medical document may be automatically classified as containing a clinical exam relevant to a HEDIS metric. This allows for accurate record keeping and reporting by clinicians to institutions such as the National Committee for Quality Assurance. Further, by visually explaining the medical document classification, the methods and systems described in the present disclosure increase compliance and provide assurance to the clinician. In some variation, the clinician's "proof-reading" of the medical document may increase reliability of the document classification by providing a human audit. This feedback mechanism may allow any potential errors in the method and system to be rapidly identified and improved upon. Yet another advantage is reducing administrative burden and/or clinical burnout, by optimizing routine manual document review processes via automatic visual highlighting of the most relevant texts within an extensive medical document. Consequently time, labor, and cost savings are realized, and ultimately, medical care is improved.

Methods for Processing Documents

Figure 1:
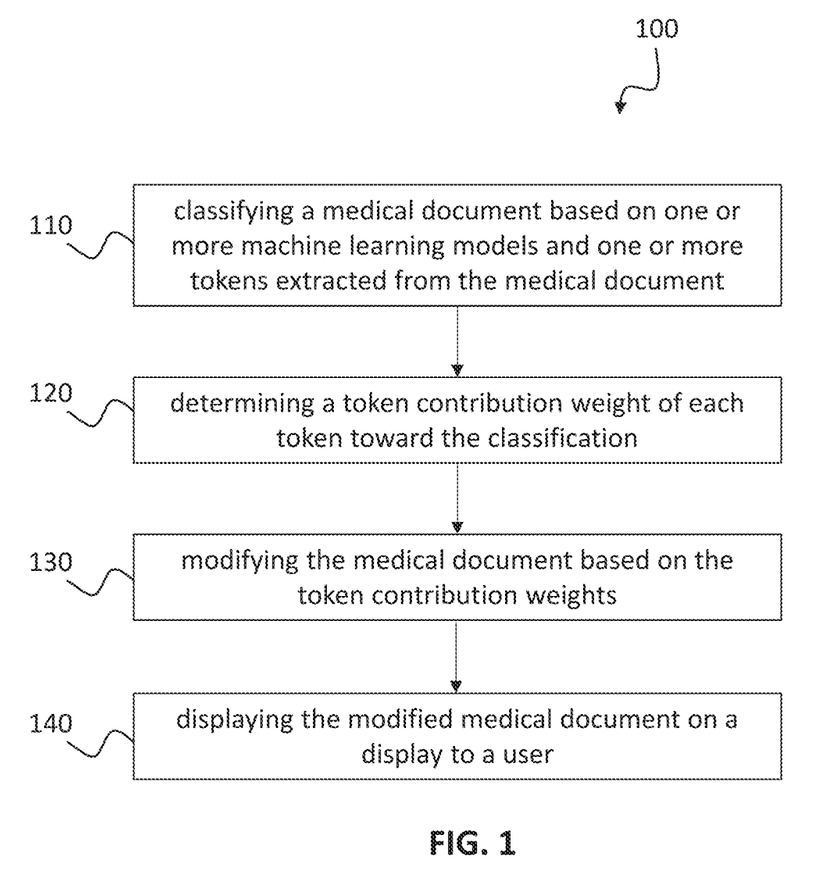
FIG. 1 depicts an illustrative flowchart of an example of a method for automatically processing a medical document.

As shown in FIG. 1, a method 100 for automatically processing a document may include classifying a medical document based on one or more machine learning models and one ore more tokens extracted from the medical document 110, determining a token contribution weight of each token toward the classification 120, modifying the medical document based on the token contribution weights 130, and displaying the modified medical document on a display to a user 140.

Document Classification

Figure 2:
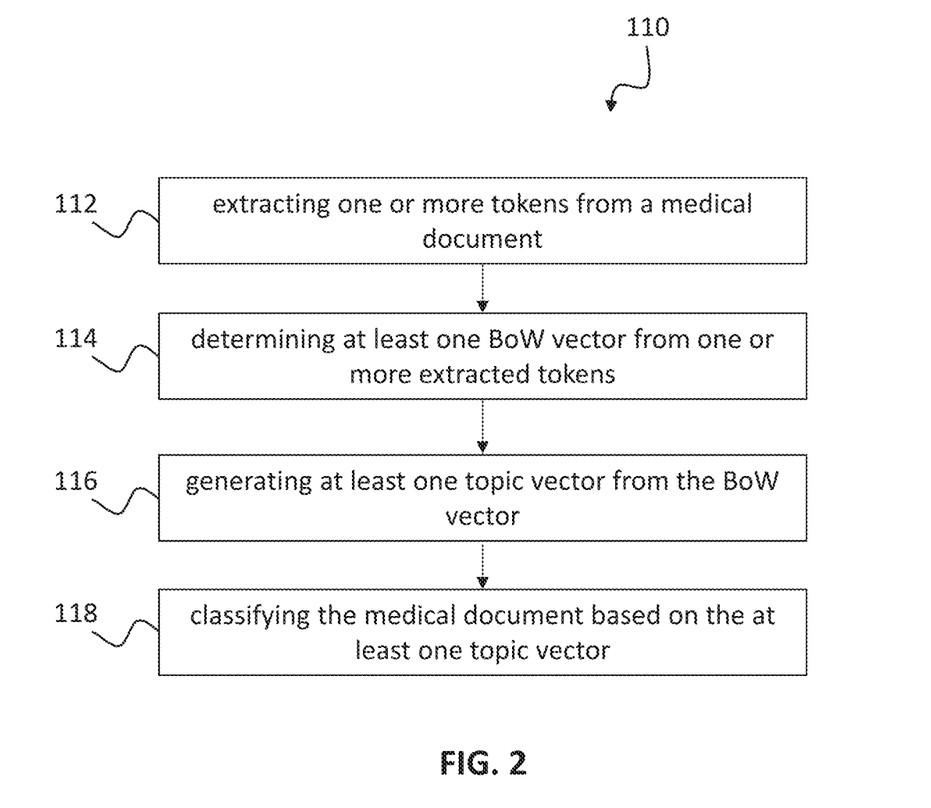
FIG. 2 depicts an illustrative flowchart of an example of a method for classifying a medical document.

Classification of a document (e.g., a medical document may function to label the document as a document of one or more types. As shown in FIG. 2, classifying a document may include extracting one or more tokens from the document (112), determining at least one Bag of Words (BoW) vector from one or more extracted tokens (114), generating at least one topic vector from the BoW vector (116), and classifying document based on the at least one topic vector (118).

Figure 4A:
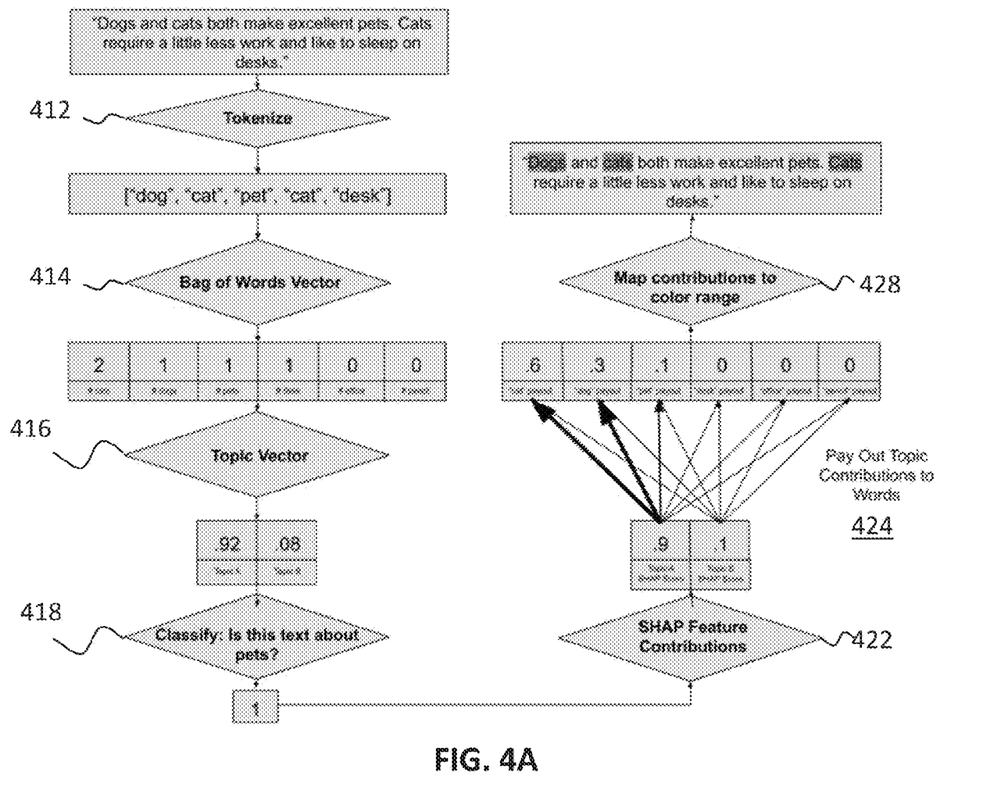
FIG. 4A depicts an example of a method for automatically processing a document.

As an illustrative example of this process, FIG. 4A refers to a document containing a text from which a tokenizing algorithm may extract tokens such as "dog", "cat", "pet" and "desk" (412). The tokenizing algorithm may, for example split the text string into a list of tokens by removing punctuation, stemming, stop words, etc. From the one or more extracted tokens, at least one Bag of Words (BoW) vector may be determined (414). As illustrated in FIG. 4A, a BoW model may be used to compute BoW vectors based on the tokens identified above. The BoW vector may keep count of the total occurrence of the tokens as they appeared in the text. Thus, the BoW vector "cats" may be assigned a value of 2, "dogs", "pets" and "desk" may be assigned a value of 1, and "office and "pencil" may be assigned a value of 0. From the BoW vectors, at least one topic vector may be generated (416). In some variations, the at least one topic vector may be generated, for example, by fitting a Latent Dirichlet Allocation model that reduces the dimensionality of BoW vector to topic vectors. Each topic feature or slot corresponds to a topic, such as Topic A for pets, and Topic B for office supplies. The number displayed in each topic feature or slot, i.e. 0.92 for Topic A (pets) and 0.08 for Topic B (office supplies), maps to a probability distribution of tokens for that topic. The document may be then be classified based on the at least one topic vector (418). In some variations, the medical document may be classified by applying, for example, a gradient boosting classifier model to the at least one topic vector. In some variations, the classifier model may also output a confidence level toward the predicted label. In the example illustrated in FIG. 4A, gradient boosting classifier model was used to predict a label of 1 (positive) or 0 (negative) for text based on topic vector. Thus, the text was classified with a label of 1 as being about Topic A (i.e., pets).

Explainability Technique

Figure 3:
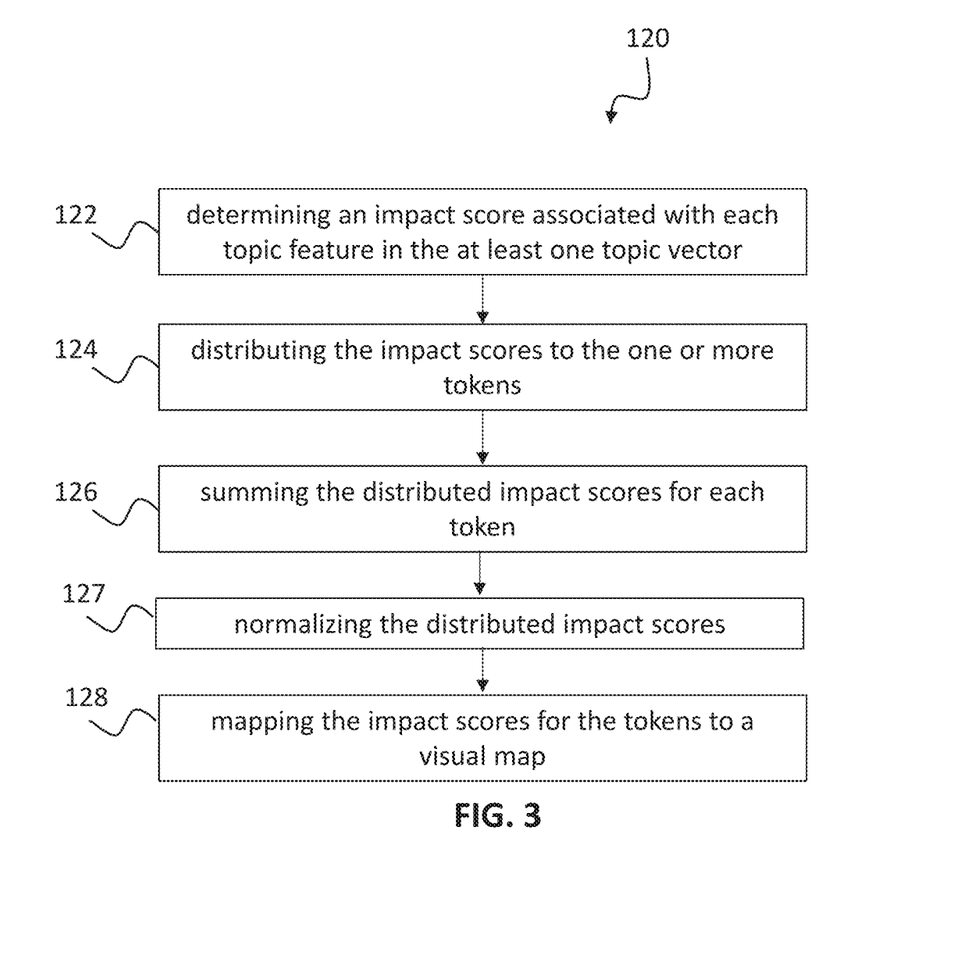
FIG. 3 depicts an illustrative flowchart of an example of a method for determining a token contribution weight.

Task-specific highlighting of text may rely on an explainability technique that explains the classification of a document as described above. To explain classification of documents, for example medical documents, token contribution weight of each token toward the classification may be determined. As shown in FIG. 3, determining a token contribution weight of each token toward the classification may include determining an impact score associated with each topic features in the topic vector (122), distributing the impact scores to the one or more tokens (124), and summing the distributed impact scores for each token (126). The impact score may, for example, be a Shapley Additive Explanation (SHAP) value for each previously-identified topic feature. SHAP values account for both magnitude and direction, for instance a positive SHAP value for a topic feature means that the topic feature pushed the classifier towards the predicted label, while a negative value means the topic feature pushed the classifier away from a particular predicted label. Accordingly, in some variations, distributing the impact scores to the one or more tokens (124) may include distributing the SHAP values of each topic features to all of the tokens.

The method may further include mapping the impact scores for the tokens to a visual map (128), such as a color map. The visual map may, for example, visually highlight or otherwise provide a visual indication of which tokens (e.g., words) contributed strongly to the document classification. In one example, the visual map may be a color map (e.g., temperature map) where tokens found to contribute strongly to the document classification (based on determined token contribution weight) may be associated with a first color (e.g., red), while tokens found to not contribute strongly to the document classification may be associated with a second color (e.g., blue). The color map may correspond to a spectrum (e.g., ranging from dark blue to dark red, with intermediate intensities and/or colors to be associated with moderate contributions to the document classification). In some variations, the per-token contribution weights may be normalized (127) such as prior to mapping (128), such that the maximum value is the output of the model. For example, the contributions may be scaled to between −1 and 1, where 1 is a very confident positive prediction, while −1 is a very confident negative prediction. The visual map may be scaled accordingly to such normalized contribution weights. For example, a contribution weight of 1 may be mapped to one extreme of the color map (e.g., dark red).

In some variations, the visual map may be scaled based on the confidence level of the classification of the medical document. For example, if the document was classified as a particular type with only 50% confidence, then a map scale otherwise ranging from −1 to 1 may be scaled by half (i.e., −0.5 to −0.5).

Additionally or alternatively, visual mapping may be include one or more discrete thresholds or "buckets". For example, in some variations, only tokens having a token contribution weight exceeding a predetermined threshold (e.g., 0.6, 0.7, 0.8, 0.9, etc.) may be mapped to a particular color. As another example, in some variations, only tokens having a token contribution weight falling within a first range of values (e.g., between 0.7 and 0.9) may be mapped to a first color, while tokens having a token contribution weight falling within a second range of values (e.g., between 0.5 and 0.7) may be mapped to a second color, and so forth.

In some variations, the distributed token contribution weights may be summed prior to mapping, such as on a sentence-level (or partial sentence, such as phrases between punctuation, etc.). The summed token contribution weights may also be mapped and/or thresholded to a visual map as described above. One advantage of mapping such summed impact scores among phrases or sentences is to produce smoother highlighting that may be more intuitive for a human reader. For example, summing token weights at the sentence level may enable highlighting of an entire important sentence, rather than discretely and/or intermittently highlighting individual words. Furthermore, in some variations the per-sentence contributions may be normalized such that the maximum value is the output score of the model. For example, the contributions may be scaled to between 0 and 1, where 1 is a very confident positive prediction, while 0 is a very confident negative prediction.

Figure 4B:
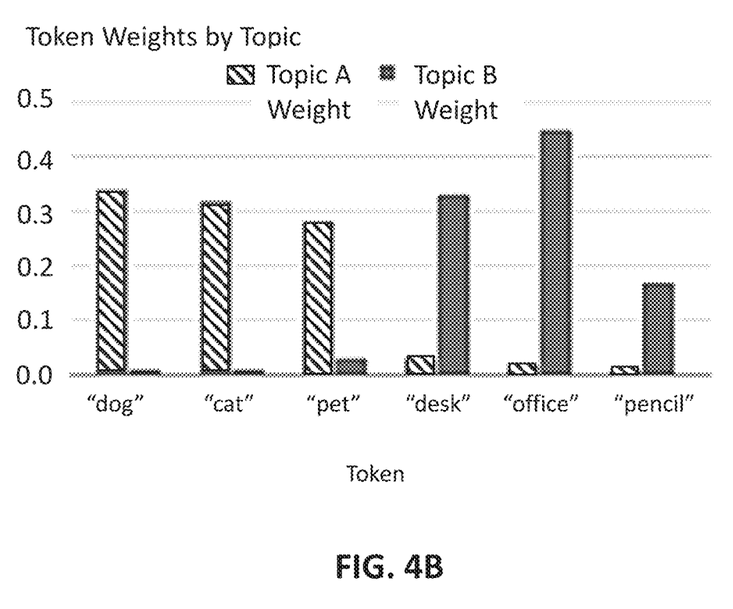
FIG. 4B depicts token weights in the example method shown in FIG. 4A.

FIG. 4A provides an illustrative example of the above-described explainability technique for an example document. As shown in FIG. 4A, an impact score associated with each topic feature in the at least one topic vector may be determined (422). In some variations, the impact score may be a Shapley Additive Explanation (SHAP) value for the previously-identified topic features. As described above, SHAP values account for both magnitude and direction, for instance a positive SHAP value for a topic feature means that the topic feature pushed the classifier towards the predicted label, while a negative value means the topic feature pushed the classifier away from a particular predicted label. Thus, the numerical values shown for Topic A (0.3) and Topic B (0.1) represent the magnitude of impact in the classifier's label conclusion. The impact scores may be distributed to the one or more tokens, and the token contribution weight for each token may be determined by summing the distributed impact scores for the token (424). As described above, in some variations the distributed impact scores may be summed at the per-sentence (or per-phrase) level and/or normalized. In some variations, the distribution of impact scores may be according to the probability distributions mapped to each topic feature in the at least one topic vector. As shown in FIG. 4A, the SHAP values for Topic A and Topic B were distributed, or "paid out", to tokens according to corresponding probability distribution for each topic feature. FIG. 4B shows token weights per topic. For example, the token "dog", which has a high probability with respect to Topic A (pets), was assigned a value of 0.3. However, the same token had negligible weight contribution to Topic B (office supplies) given the low probability.

Document Modification and Display

As shown in FIG. 1, methods for automatically processing documents (e.g., medical documents) may include modifying the medical document based on the mapping of token contribution weights (e.g., as described with respect to FIG. 3). In some variations, this may include modifying the text of the medical document based on the mapping. For example, the text font appearance and/or text font highlighting of the document may be modified based on a color mapping as described below. For example, as shown in FIG. 4A, tokens with the heaviest contribution weights ("dogs", "cats") are highlighted in dark green indicating higher contribution to the document classification as relating to pets, tokens with moderate contribution weights ("pets") are highlighted in a lighter shade of green representing its lower token contribution toward the classification. Furthermore, tokens with negative or low contribution weights ("desks") may be highlighted in an even lighter shade of green than those with moderate contribution weights. Similarly, entire sentences or phrases may be highlighted based on summed token weights, summed as described above. Accordingly, a modified document may be achieved by visually emphasizing portions of the text based on the determined contribution of each token(s). As shown in FIG. 1, methods for automatically processing documents may further include displaying the modified medical document to a user (140), such as on a display.

Although the visual mapping and modifications are primarily described herein as colored highlighting of text, it should be understood that emphasis of text may be accomplished through other forms of highlighting (e.g., by varying font size, font weight (e.g., degree of letter thickness), font type, font color, underlining, underline weights, etc.). In other words, the highlighting of tokens, sentences, or partial sentences may be performed in various suitable manners in order to emphasize their contribution to the classification of the document.

The methods described in the present disclosure are applicable for the classification, and explanation thereof, of any document into any one or more types. For example, the document may be a medical document, which may be classified, and the classification explained, as containing one or more healthcare metrics. In some variations, the method may be used to determine a HEDIS quality metric based on the classification, and explanation thereof, of the medical document.

EXAMPLE

FIGS. 5A and 5B relate to an example of medical document classification and explanation/highlighting suitable for use in determining a HEDIS quality metric, specifically colonoscopy screening, in the medical document.

A medical document containing a patient's medical history was obtained. FIG. 5A illustrates a portion of the medical document containing the patient's medical history. The medical document was automatically processed by the classification and explanation method described above to determine whether the medical document contained a colonoscopy test. The processed medical document is shown in FIG. 5B. The document was classified as indeed containing a colonoscopy test. Colonoscopy is classified by HEDIS as a clinical exam for screening colorectal cancer, and thus the medical document was also classified as containing a HEDIS quality metric. Further, as seen in the FIG. 5B, parts of the processed medical document were highlighted for explaining the most relevant sentences used in the classification of the document as containing colonoscopy results. The sentences shown in red were highly relevant in determining the presence of a colonoscopy test, while those in gray were somewhat unrelated or unimportant for determining the presence of a colonoscopy test.

By way of the above example, the presence of a colonoscopy test in a patient's medical record was automatically determined. The document was classified and highlighted as containing a colonoscopy test, and/or as containing a HEDIS metric for colorectal cancer screening. It is to be understood that the method of classification, and explanation thereof, of the present disclosure are applicable to any task, such as medical tasks (clinical exams, diagnostics, imaging, etc.). In some variations, the medical task could be a mammogram, which may be used to classify a medical document as positively containing a HEDIS metric for breast cancer screening. In some variations, the identified medical task, upon which one or more classification are based, may not have an associated HEDIS metric.

Systems for Processing Documents

Figure 6:
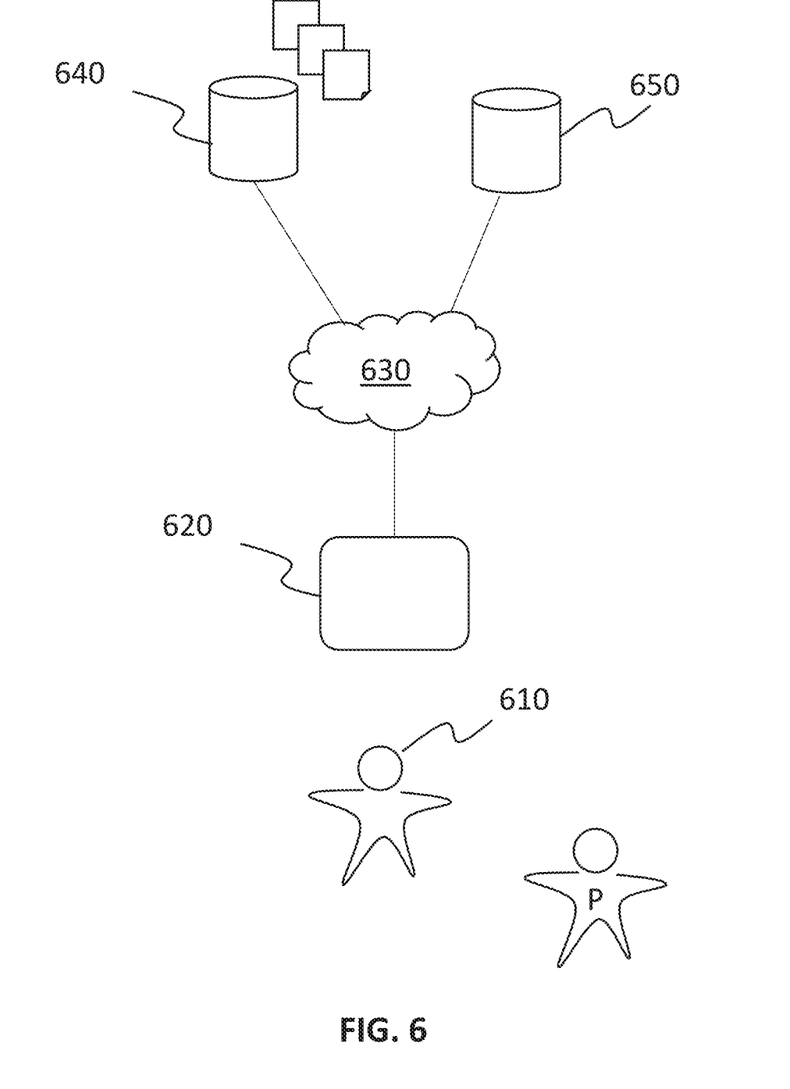
FIG. 6 depicts an illustrative schematic of a system environment with a medical document assessment system.

Generally, as shown in in FIG. 6, a clinician 610 (e.g., physician, nurse practitioner, any healthcare worker, etc.) may access a user computing device 620 for engaging with a medical document associated with a patient P. The user computing device 620 may be configured to communicate in a wireless or wired manner with a network 630 (e.g., cloud-based network or other suitable network of devices), such that data received from the user computing device 620 may be analyzed remotely (non-locally). Alternatively, data from the user computing device 620 may be analyzed locally. Also connected to the network 630 may be a document storage system 640 (e.g., server) and/or a document processing system 650, which may be accessible to the user computing device 620 over the network 630. While one particular configuration is depicted in FIG. 6 by way of example, it should be understood that other configurations for the document processing system in relation to other user interface devices are also possible.

The user computing device 620 may, for example, be a tablet, mobile phone, laptop computer, desktop computer, or the like. The user computing device may include a controller including a processor (e.g., CPU) and memory (which can include one or more computer-readable storage mediums). The processor may incorporate data received from memory and user input. The memory may include stored instructions to cause the processor to execute modules, processes, and/or functions associated with the methods described herein. In some variations, the memory and processor may be implemented on a single chip, while in other variations they can be implanted on separate chips.

In some variations, the user computing device may further include a communication interface configured to permit a clinician or other user to control the computing device. The communication interface may include a user interface configured to permit a user (e.g., patient, health care professional, etc.) to control the computing device. The communication interface may permit a user to interact with and/or control a computing device directly and/or remotely. For example, a user interface of the computing device may include an input device for a user to input commands and an output device for a user to receive output (e.g., prompts on a display device).

The communication interface may further include a network interface configured to connect the computing device to another system (e.g., internet, remote server, database) by wired or wireless connection. In some variations, the computing device may be in communication with other devices via one or more wired or wireless networks. In some variations, the communication interface may include a radiofrequency receiver, transmitter, and/or optical (e.g., infrared) receiver and transmitter configured to communicate with one or more devices and/or networks.

For example, the communication interface may enable the user computing device to communicate with the document storage system 640 and/or document processing system 650 over a network 630, as shown in FIG. 6. The document storage system 640 may include, for example, a HIPAA-compliant server configured to store and enable access to the medical documents.

Figure 7:
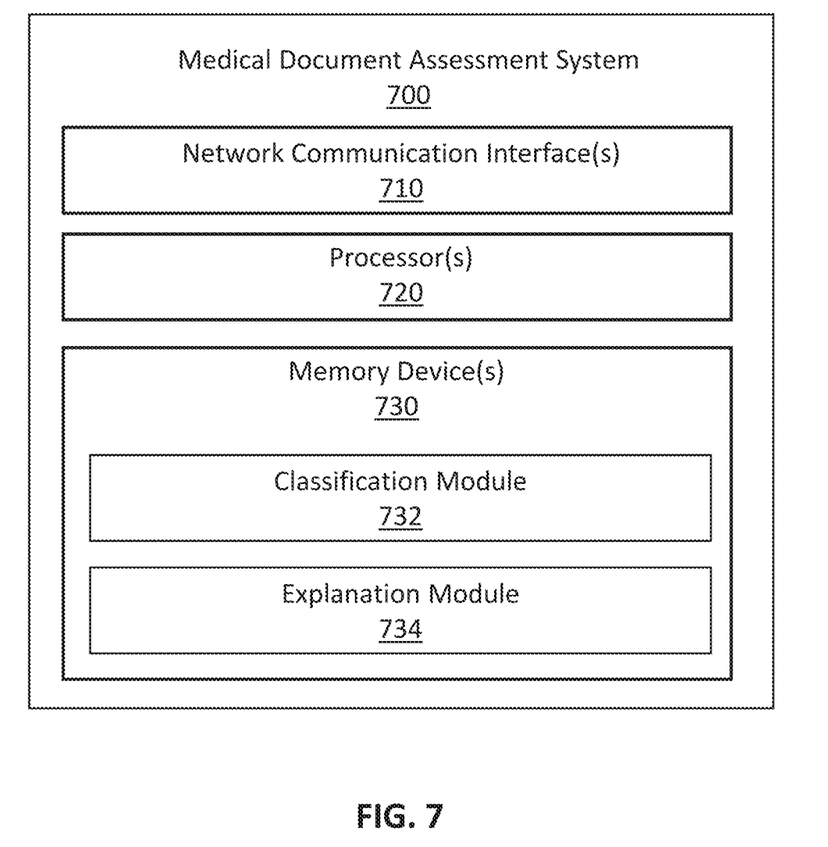
FIG. 7 depicts an illustrative schematic of an exemplary medical document assessment system.

As shown in FIG. 7, the medical document assessment system 700 may include one or more processors 720 which may be configured to execute instructions stored on one or more memory devices 730. The medical document assessment system 700 may further include one or more network communication interfaces 710 to transmit and/or receive data such as medical documents to and from user computing devices, etc.

The medical document assessment system 700 may include one or more processors configured to perform one or more aspects of the methods described above. For example, the system 700 may include one or more processors configured to receive a medical document and classify the medical document as one or more document types. The one or more processors may be further configured to modify the medical document and display the modified medical document to a clinician. For example, the one or more processors may be configured to perform any one or more of the processes described above with respect to FIG. 1, such as to determine a token contribution weight of each token toward the classification, modify the medical document based on the token contribution weights, and display the modified medical document on a display to a user.

For example, as shown in FIG. 7, the one or more memory devices 730 may include software encoding an a classification module 732 configured to receive one or more medical documents and classify the medical documents based on one or more machine learning models and one or more tokens extracted from the medical document. In some variations, one or more processors executing software encoding the classification module 732 may, for example, be configured to perform any one or more of the processes described above with respect to FIGS. 1 and 2. For example, the one or more processors may be configured to extract one or more tokens from a medical document, determine at least one BoW vector from one or more extracted tokens, generate at least one topic vector from the BoW vector, and/or classify the medical document based on the at least one topic vector.

Furthermore, as shown in FIG. 7, the one or more memory devices 730 may include software encoding an explanation module 734 configured to modify and display the modified medical document. In some variations, one or more processors executing software encoding the explanation module 734 may, for example, may be configured to perform any one or more of the explanation processes described above with respect to FIG. 1 and FIG. 3. In some variations, one or more processors may be configured to determine an impact score associated with each topic feature in at least one topic vector, distribute the impact scores to the one or more tokens, sum the distributed impact scores for each token, normalize the distributed impact scores, and/or map the impact scores for the tokens to a visual map. In some variations, the one or more processors may map the token contribution weights to a color map, for example.

One or more processors may be further configured to modify text of the medical document based on the mapping. For example, the medical document may be modified at least in part by changing at least one of text font appearance and text font highlighting based on the mapping. Further, in some variations, the medical document may be modified at least in part by determining a sentence contribution weight of each sentence in the medical document based on the sum of token contribution weights of one or more tokens in the sentence and mapping the sentence contribution weights to a color map or other visual map. The modified medical document may be displayed to a user on a display.

The classified and modified medical documents may be communicated to a user computing device 620 through one or more network communication interfaces. The user computing device 620 may then be configured to provide a classification of the medical document into one or more types along with explanation of the classification, for example by highlighting relevant words and/or sentences in the modified medical document. Examples of medical documents with classification and highlighting are shown and described above with respect to FIGS. 5A and 5B.

The systems described in the present disclosure are applicable for the classification of any documents into any one or more types. For example, the document may be a medical document which may be classified as containing one or more metrics. In some variations, the classification may be used to determine a HEDIS quality metric based on the classification of the medical document.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to explain the principles of the invention and its practical applications, they thereby enable others skilled in the art to utilize the invention and various embodiments with various modifications as are suited to the particular use contemplated. It is intended that the following claims and their equivalents define the scope of the invention.

The invention claimed is:

1. A computer-implemented method comprising:
generating a classification of a medical document as one or more document types based at least in part on one or more machine learning models and one or more tokens extracted from the medical document;
determining a contribution weight of a phrase or a sentence in the medical document toward the classification based on a sum of token contribution weights of tokens in the phrase or the sentence;
modifying the medical document, wherein the phrase or the sentence is modified to reflect a degree of visual emphasis based on the contribution weight of the phrase or the sentence; and
causing display of the modified medical document.

2. The computer-implemented method of claim 1, wherein generating the classification comprises classifying the medical document as including text relating to a particular medical event.

3. The computer-implemented method of claim 2, wherein the medical event is a clinical exam.

4. The computer-implemented method of claim 1, wherein generating the classification comprises:
determining at least one bag of words vector from one or more extracted tokens;
generating at least one topic vector from the at least one bag of words vector, wherein the at least one topic vector comprises one or more topic features, each topic feature mapping to a probability distribution of tokens for the topic feature; and
classifying the medical document based on the at least one topic vector.

5. The computer-implemented method of claim 4, wherein generating at least one topic vector comprises fitting a Latent Dirichlet Allocation model to the at least one bag of words vector.

6. The computer-implemented method of claim 4, wherein classifying the medical document comprises applying a gradient boosting classifier model to the at least one topic vector.

7. The computer-implemented method of claim 4, further comprising:

determining an impact score associated with each topic feature in the at least one topic vector;

distributing the impact scores to the one or more tokens according to the probability distributions mapped to each topic feature in the at least one topic vector; and determining a token contribution weight for each token by summing the distributed impact scores for the token.

8. The computer-implemented method of claim 7, wherein the impact score is a Shapley Additive Explanation (SHAP) value, and wherein distributing the impact scores to the one or more tokens comprises distributing the SHAP value of each topic feature to all of the one or more tokens, and normalizing the distributed SHAP values.

9. The computer-implemented method of claim 1, wherein modifying the medical document comprises mapping the contribution weight to a color map, and modifying text of the medical document based on the mapping.

10. The computer-implemented method of claim 9, wherein modifying the medical document comprises at least one of:
changing at least one of text font appearance and text font highlighting based on the mapping; and
scaling the color map based on a confidence level of the classification of the medical document.

11. The computer-implemented method of claim 1, further comprising determining a HEDIS quality metric based at least in part on the classification of the medical document.

12. A system comprising:
one or more processors; and
memory storing one or more instructions that, when executed by the one or more processors, cause the system to perform operations comprising:
generating a classification of a medical document as one or more document types based at least in part on one or more machine learning models and one or more tokens extracted from the medical document;
determining a contribution weight of a phrase or a sentence in the medical document toward the classification based on a sum of token contribution weights of tokens in the phrase or the sentence;
modifying the medical document, wherein the phrase or the sentence is modified to reflect a degree of visual emphasis based on the contribution weight of the phrase or the sentence; and
causing display of the modified medical document.

13. The system of claim 12, wherein generating the classification comprises:
determining at least one bag of words vector from one or more extracted tokens;
generating at least one topic vector from the at least one bag of words vector, wherein the at least one topic vector comprises one or more topic features, each topic feature mapping to a probability distribution of tokens for the topic feature; and
classifying the medical document based on the at least one topic vector.

14. The system of claim 13, wherein the operations further comprise:

determining an impact score associated with each topic feature in the at least one topic vector;

distributing the impact scores to the one or more tokens according to the probability distributions mapped to each topic feature in the at least one topic vector; and determining a token contribution weight for each token by summing the distributed impact scores for the token.

15. The system of claim 12, wherein modifying the medical document comprises mapping the contribution weight to a color map, and at least one of modifying text of the medical document based on the mapping, and changing at least one of text font appearance and text font highlighting based on the mapping.

16. A non-transitory computer-readable storage medium including instructions that, when executed, cause a computing system to perform operations comprising:
generating a classification of a medical document as one or more document types based at least in part on one or more machine learning models and one or more tokens extracted from the medical document;
determining a token contribution weight of a phrase or a sentence in the medical document toward the classification based on a sum of token contribution weights of tokens in the phrase or the sentence;
modifying the medical document, wherein the phrase or the sentence is modified to reflect a degree of visual emphasis based on the contribution weight of the phrase or the sentence; and
causing display of the modified medical document on a display.

17. The non-transitory computer-readable storage medium of claim 16, wherein the operations further comprise:
determining an impact score associated with each topic feature in the at least one topic vector;
distributing the impact scores to the one or more tokens according to the probability distributions mapped to each topic feature in the at least one topic vector; and
determining a token contribution weight for each token by summing the distributed impact scores for the token.

18. The non-transitory computer-readable storage medium of claim 16, wherein modifying the medical document comprises mapping the contribution weight to a color map, and at least one of modifying text of the medical document based on the mapping, and changing at least one of text font appearance and text font highlighting based on the mapping.

19. The system of claim 12, wherein generating the classification comprises classifying the medical document as including text relating to a particular medical event, and the medical event is a clinical exam.

20. The non-transitory computer-readable storage medium of claim 16, wherein generating the classification comprises classifying the medical document as including text relating to a particular medical event, and the medical event is a clinical exam.

* * * * *